(12) United States Patent
Sage

(10) Patent No.: US 8,512,312 B2
(45) Date of Patent: Aug. 20, 2013

(54) OFFSET CATHETER CONNECTOR, SYSTEM AND METHOD

(75) Inventor: Shahn S. Sage, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1150 days.

(21) Appl. No.: 11/799,167

(22) Filed: May 1, 2007

(65) Prior Publication Data

US 2008/0275429 A1 Nov. 6, 2008

(51) Int. Cl.
*A61M 25/16* (2006.01)
*A61M 25/18* (2006.01)
*A61M 31/00* (2006.01)

(52) U.S. Cl.
USPC .......................................... 604/535; 604/513

(58) Field of Classification Search
USPC ........................ 604/533–539, 513; 285/417
See application file for complete search history.

(56) References Cited

U.S. PATENT DOCUMENTS

| | | | |
|---|---|---|---|
| 3,482,857 A * | 12/1969 | Gohs ........................ | 285/148.27 |
| 4,192,532 A | 3/1980 | Pacella | |
| 4,329,076 A * | 5/1982 | Coreth ....................... | 403/109.8 |
| 4,592,749 A | 6/1986 | Ebling et al. | |
| 4,635,972 A * | 1/1987 | Lyall .......................... | 285/242 |
| 4,834,719 A | 5/1989 | Arenas | |
| 4,929,236 A | 5/1990 | Sampson | |
| 4,963,133 A | 10/1990 | Whipple | |
| 5,053,015 A | 10/1991 | Gross | |
| 5,129,891 A | 7/1992 | Young | |
| 5,163,921 A * | 11/1992 | Feiring ......................... | 604/247 |
| 5,226,898 A | 7/1993 | Gross | |
| 5,356,381 A | 10/1994 | Ensminger et al. | |
| 5,405,339 A | 4/1995 | Kohnen et al. | |
| 5,637,102 A | 6/1997 | Tolkoff et al. | |
| 5,827,242 A | 10/1998 | Follmer et al. | |
| 5,931,829 A | 8/1999 | Burbank et al. | |
| 6,308,992 B1 | 10/2001 | Mitsui et al. | |
| 6,508,806 B1 | 1/2003 | Hoste | |
| 6,817,995 B1 | 11/2004 | Halpern | |
| 6,868,773 B2 | 3/2005 | Davis et al. | |
| 6,910,906 B2 | 6/2005 | Schorn | |
| 6,971,390 B1 * | 12/2005 | Vasek et al. .................. | 604/533 |
| 6,997,919 B2 | 2/2006 | Olsen et al. | |

(Continued)

FOREIGN PATENT DOCUMENTS

EP 0 343 910 A2 11/1989
EP 0 343 910 A3 2/1990

(Continued)

OTHER PUBLICATIONS

U.S. Appl. No. 11/799,165, filed May 1, 2007, Sage et al.

*Primary Examiner* — Kevin C Sirmons
*Assistant Examiner* — Bradley Osinski
(74) *Attorney, Agent, or Firm* — Mueting, Raasch & Gebhardt, P.A.

(57) ABSTRACT

Catheter connectors, connection systems, and methods of use in which a catheter is attached to an offset connector such that the catheter is retained on the connector by compression between a tube located within the catheter and a collar fitted over the portion of the catheter containing the tube. The catheters used with the offset catheter connection systems may include an elastically compressible inner body that is surrounded by a reinforcing braid. After the offset connector tube is inserted into the lumen of the catheter, a collar may be advanced over the exterior of the catheter and the offset connecter tube contained therein.

28 Claims, 5 Drawing Sheets

(56) References Cited

U.S. PATENT DOCUMENTS

| | | |
|---|---|---|
| 2003/0199853 A1 | 10/2003 | Olsen et al. |
| 2004/0153049 A1 | 8/2004 | Hewitt et al. |
| 2004/0181208 A1 | 9/2004 | Poole |
| 2005/0085794 A1* | 4/2005 | Denoth et al. ............... 604/533 |
| 2005/0245887 A1 | 11/2005 | Olsen et al. |
| 2005/0253389 A1 | 11/2005 | Schulte |
| 2006/0084940 A1 | 4/2006 | Olsen et al. |
| 2006/0084941 A1 | 4/2006 | Olsen et al. |
| 2006/0116648 A1 | 6/2006 | Hamatake |
| 2006/0195066 A1 | 8/2006 | Cross, Jr. |

FOREIGN PATENT DOCUMENTS

| | | |
|---|---|---|
| EP | 0 343 910 B1 | 6/1993 |
| EP | 1 078 645 A2 | 2/2001 |
| EP | 1 078 645 A3 | 5/2002 |
| GB | 2 318 846 A | 5/1998 |
| GB | 2 389 634 A | 12/2003 |
| WO | WO 98/24500 A1 | 6/1998 |
| WO | WO 03/030985 A2 | 4/2003 |
| WO | WO 03/030985 A3 | 7/2003 |

* cited by examiner

OFFSET CATHETER CONNECTOR, SYSTEM AND METHOD

TECHNICAL FIELD

The present invention relates generally to a medical connection system and, more particularly, to offset catheter connectors, systems, and methods.

BACKGROUND

In many medical applications, it is necessary to connect one section of medical tubing, e.g., a catheter, with another. Generally speaking, it is important that these connections be relatively secure and stable so that the catheter does not separate or develop leaks at the connection point. Security and leak-resistance take on special importance in applications where the catheter sections are implanted in a human body.

One procedure that necessitates implantation of a catheter into the body involves the use of an implantable medical device, e.g., a drug infusion pump. Such implantable medical devices are often used to control pain and/or spasticity, as well as to provide one or more drugs or fluid medications to a particular location within the body. For instance, a typical implant procedure may involve implanting a drug infusion pump into a cavity or subcutaneous pocket in the body and delivering a drug, via catheter(s), to an epidural space or intrathecal space of the spinal column or to a particular location within the brain.

A distal catheter section may be positioned in the desired location in the body and then connected to a proximal catheter section by use of a connector. The connection may be made by inserting one end or prong of the connector into a lumen of one catheter section (e.g., the proximal section) and the other end of the connector into the lumen of the other catheter section (e.g., the distal section) and then sliding both catheter sections towards one another (toward the middle of the connector). The proximal section may then be connected to the drug infusion pump.

While adequate, difficulties have been encountered in the manufacture and use of such prior art connectors. For example, an inadequate seal between the catheter and the connector may be formed during assembly or the catheters and/or connector may be damaged during assembly. Also, these connectors, which have been sized to fit within the lumens of the catheter sections, are small and may be difficult to manipulate during implantation. Moreover, because some of these connectors fit entirely within the lumens of the respective catheter sections, it is often difficult for the implanting clinician (e.g., a surgeon) to be sure that the interface between catheter sections is positioned at, or even near, the center of the connector (i.e., it may be difficult to center the catheter sections on the connector). Misalignment of the connector can result in a weakened connection that is more likely to separate and/or develop leaks. Other potential problems include: lack of ability to adequately secure the catheters relative to one another; and inability to provide sufficient strain relief to the connection.

SUMMARY OF THE INVENTION

The present invention provides catheter connectors, connection systems, and methods in which a catheter is attached to an offset connector such that the catheter is retained on the connector by compression between a tube located within the catheter and a collar fitted over the portion of the catheter containing the tube.

The catheters used with the offset catheter connectors may include an elastically compressible inner body that is surrounded by a reinforcing braid. After the offset connector tube is inserted into the lumen of the catheter, a collar may be advanced over the exterior of the catheter and the offset connecter tube contained therein. Because the passage in which the catheter is located is offset relative to the tube located in the catheter, the catheter is compressed within the collar passage between the tube and the collar passage. Due to the offset between the tube and the collar passage, the catheter may be differentially compressed on opposing sides of the tube.

In one aspect, the present invention provides a catheter connection system having a connector body and a first tube extending from the connector body. The first tube includes a bore extending through the first tube, and wherein the first tube defines a first tube axis centered within and extending through the first tube. The connection system may also include a first catheter having an end portion attached to the first tube, wherein the end portion of the first catheter has a lumen that is occupied by the first tube; and a first collar attached to the connector body, wherein the first collar has a first passage, wherein the first passage defines a first passage axis centered within and extending through the first passage, and wherein the end portion of the first catheter and the first tube are located within the first passage, and wherein the first passage axis is offset from the first tube axis when the first collar is attached to the connector body. In use, the end portion of the first catheter is differentially compressed on opposing sides between a portion of an outer surface of the first tube and a portion of an inner surface of the first passage.

In various aspects, the catheter connection systems may optionally include one or more of the following features: the first tube axis may be parallel to the first passage axis; the bore in the first tube may be centered along the first tube axis; the connector body may be a circular cylindrical connector body defining a central axis, wherein the first tube axis is offset from the central axis; the connector body may be a circular cylindrical connector body defining a central axis, wherein the first passage axis is coincident with the central axis when the first collar is attached to the connector body; the first tube may have a uniform cross-sectional profile along its length; the first passage in the first collar may have a uniform cross-sectional profile along its length; the first tube may be located entirely within the first passage when the first collar is attached to the connector body; the connector body and the first collar may include a retention mechanism located between the first collar to the connector body, wherein the retention mechanism may be a ratchet connection; etc. The catheter may include an elastically compressible inner body that is surrounded by a reinforcing braid located around an outer surface of the inner body, wherein the reinforcing braid and the inner body are surrounded by an optional outer sheath covering the outer surface of the inner body and the reinforcing braid, wherein the inner body is differentially compressed between the first tube and the first passage.

The catheter connection systems of the present invention may further include a second tube extending from the connector body, wherein the second tube may include any combination of the features described in connection with the first tube. Furthermore, the first tube and the second tube may be aligned such that the first tube axis and the second tube axis are coincident with each other. In some embodiments, the first tube and the second tube may be portions of a common tube that extends through the connector body.

In another aspect, the present invention provides method of connecting a catheter to a connection system, the method including inserting a first tube into a lumen at an end of a first catheter such that the first tube occupies an end portion of the catheter, wherein the first tube extends from a connector body, and further wherein the first tube includes a bore extending through the first tube and a first tube axis centered within and extending through the first tube. The method further includes differentially compressing opposing sides of the catheter within the end portion of the catheter by attaching a first collar to the connector body, wherein the compression occurs between the first tube and a first passage of the first collar, wherein the first passage defines a first passage axis centered within and extending through the first passage, and wherein the end portion of the first catheter and the first tube occupying the end portion of the first catheter are located within the first passage, and wherein the first passage axis is offset from the first tube axis when the first collar is attached to the connector body.

In another aspect, the present invention provides a therapeutic substance delivery system that includes an implantable therapeutic substance delivery device; a delivery catheter and a catheter connector connecting the delivery catheter to the implantable medical device. The catheter connector includes a connector body; a first tube extending from the connector body, wherein the first tube includes a bore extending through the first tube, and wherein the first tube defines a first tube axis centered within and extending through the first tube, wherein an end portion of the delivery catheter includes a lumen that is occupied by the first tube; and a first collar attached to the connector body, wherein the first collar has a first passage, wherein the first passage defines a first passage axis centered within and extending through the first passage, and wherein the end portion of the delivery catheter and the first tube are located within the first passage, and wherein the first passage axis is offset from the first tube axis when the first collar is attached to the connector body; wherein the end portion of the delivery catheter occupied by the first tube is differentially compressed on opposing sides between a portion of an outer surface of the first tube and a portion of an inner surface of the first passage.

In another aspect, the therapeutic substance delivery system may include a proximal catheter located between the implantable therapeutic substance delivery device and the catheter connector, wherein the catheter connector further includes a second tube extending from the connector body, wherein the second tube has a bore extending through the second tube, and wherein the second tube defines a second tube axis centered within and extending through the second tube, and wherein an end portion of the proximal catheter includes a lumen that is occupied by the second tube; and a second collar attached to the connector body, wherein the second collar has a second passage, wherein the second passage defines a second passage axis centered within and extending through the second passage, and wherein the end portion of the proximal catheter and the second tube are located within the second passage, and wherein the second passage axis is offset from the second tube axis when the second collar is attached to the connector body. The end portion of the proximal catheter occupied by the second tube is differentially compressed on opposing sides between a portion of an outer surface of the second tube and a portion of an inner surface of the second passage.

The above summary is not intended to describe each embodiment or every implementation of the present invention. Rather, a more complete understanding of the invention will become apparent and appreciated by reference to the following Detailed Description of Illustrative Embodiments and claims in view of the accompanying figures of the drawing.

BRIEF DESCRIPTION OF THE VIEWS OF THE DRAWING

The present invention will be further described with reference to the views of the drawing, wherein.

DETAILED DESCRIPTION OF ILLUSTRATIVE EMBODIMENTS

Figure 1:
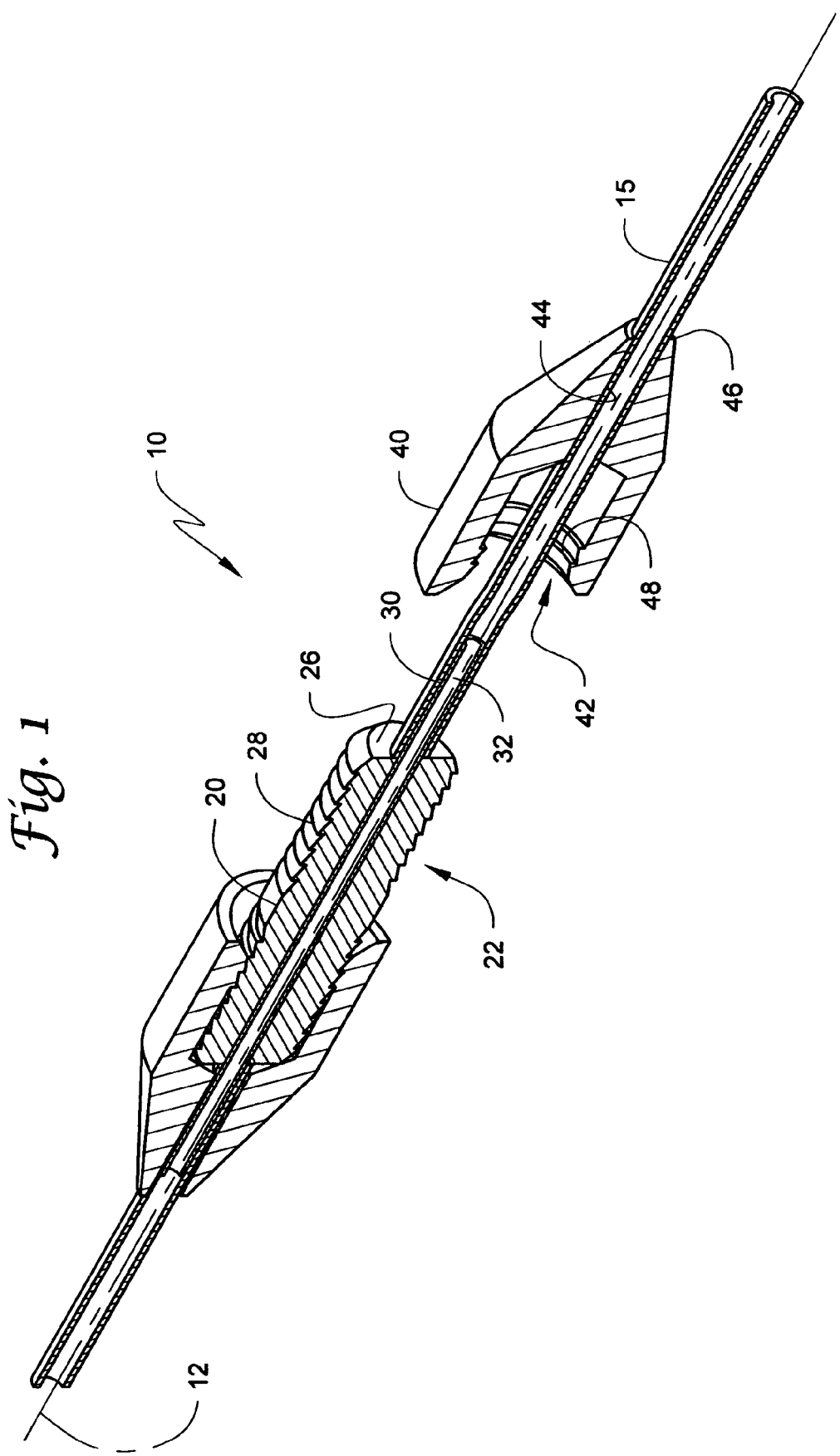
FIG. 1 is a cross-sectional, perspective view of one illustrative catheter connection system according to the present invention.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

As used herein, "a," "an," "the," "at least one," and "one or more" are used interchangeably. The term "and/or" (if used) means one or all of the listed elements or a combination of any two or more of the listed elements.

FIGS. 1-5 are different views of one illustrative offset catheter connection system 10 used to connect catheters according to the present invention. The offset catheter connection system 10 may include a connector body 20, a connector tube 30, a collar 40, and a catheter 50, with the components being arranged along a longitudinal axis 12 that extends through the different components of the system 10.

Although the connector body 20 depicted in FIGS. 1-5 is a two-sided offset connector, i.e., it includes offset connector structures on each of two ends, connector bodies of the invention may include only one side that includes an offset connector as described herein. A single-sided connector body may, for example, be formed as integral component of, e.g., a pump or other device to which a catheter is to be connected.

In other embodiments, the connector bodies of the present invention may be two-sided, but include different connector structures on the two ends. For example, one side of the connector body may include an offset connector (examples of which are described herein), while the other side of the connector body may include a different connector structure. Examples of some potentially suitable connector structures may be described in, e.g., U.S. Pat. Nos. 4,929,236 (Sampson); 4,963,133 (Whipple); 5,129,891 (Young); 5,637,102 (Tolkoff et al.); 5,405,339 (Kohnen et al.); and 6,910,906 (Schorn). Still other potentially suitable connector structures may be described in U.S. Patent Application Publication Nos. US 2005/0253389 (Schulte) and US 2006/0195066 (Cross, Jr.).

Furthermore, the connector bodies on which offset connector structures may be provided may include more than two connector structures. For example, the connector bodies may include three or more connector structures, one or more of which may be offset connector structures as described herein. One example of a connector body that includes three connector structures is described in, e.g., U.S. Patent Application Publication No. US 2005/0245887 (Olsen et al.).

The connector body 20 of the connection system depicted in FIGS. 1-5 has a circular cross-sectional shape, although any suitable cross-sectional shape may alternatively be used (e.g., octagonal, elliptical, oval, etc.) for the connector body 20. Regardless of the shape of the connector body 20, the collars 40 used with the connector body 20 have a complementary shape such that they can be attached to the connector body 20 as described herein.

In the depicted system 10, longitudinal axis 12 extends through the center of the connector body 20. In other words, the depicted circular cylindrical connector body 20 defines a central axis that is coincident with longitudinal axis 12. In other embodiments, however, the longitudinal axis 12 may not be coincident with the central axis of the connector body 20.

As discussed herein, the catheter connection system depicted in FIGS. 1-5 includes a connector tube 30 that extends from two sides of the connector body 20 (although in a one-sided connector, a tube would extend only from one side of the body). In the interest of brevity, only one side of the connection system will be described herein, with the understanding that the opposite end of the connection system 10 includes the same or similar features.

The tube 30 extending from the connector body 20 is hollow and includes a bore 32 extending through the tube 30 such that fluids can pass through the tube from one end to the other. It is the bore 32 in the tube 30 through which fluids pass between catheters attached using the catheter connection system of FIGS. 1-5. In use, a catheter is fitted over the tube 30 such that the tube 30 is located within the catheter lumen.

Figure 2:
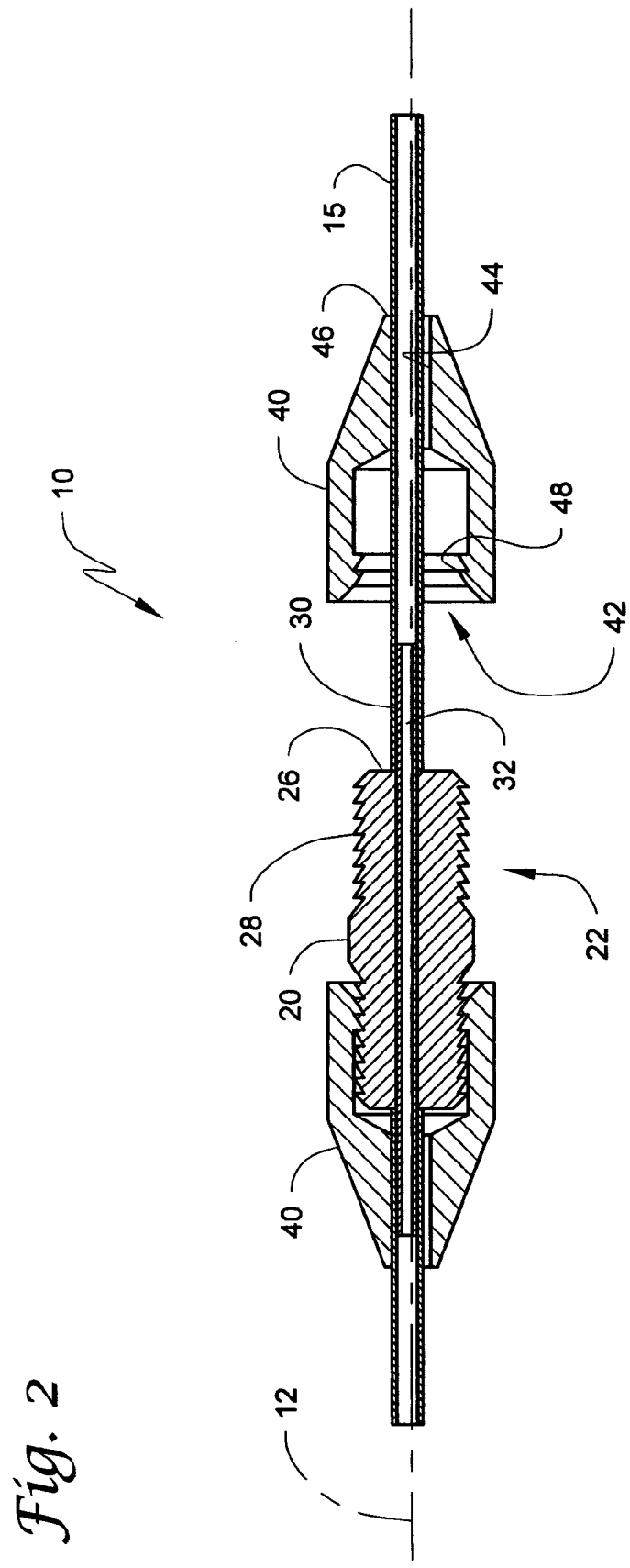
FIG. 2 is a cross-sectional, side view of the catheter connection system taken along the longitudinal axis of FIG. 1.
Figure 4:
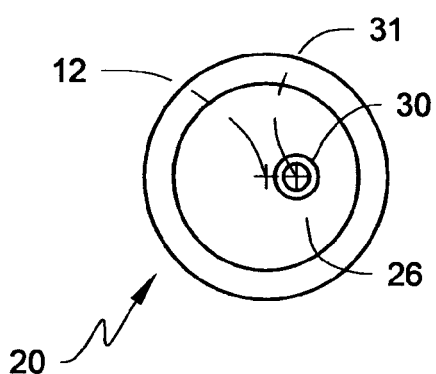
FIG. 4 is an end view of the connector body of the catheter connection system of FIG. 1.

In the depicted embodiment, the tube 30 extends out of the connector body 20 from a stop surface 26. The stop surface 26 of the connector body 20 depicted in FIGS. 1, 2, & 4 is flat and generally perpendicular to the axis 12. The stop surface 26, however, may take any other suitable shape or orientation. The stop surface 26 may provide a positive stop against which the ends of the catheters 15 abut when attaching catheters 15 to the connector body 20. Advancement of catheters, e.g., catheter 15, on the connector tube 30 past the stop surface 26 may be difficult, if not impossible.

The connector tube 30 may extend beyond the ends (or end in the case of a single-sided connector) of the connector body 20 by any suitable distance that can provide a secure catheter connection. It may, however, be beneficial if the tube 30 remains within the passage 44 of the collar 40 as described herein.

Although the depicted tube 30 has a circular cross-sectional shape, the connector tubes used in the connection systems of the present invention may take any suitable shape (e.g., octagonal, elliptical, oval, etc.). Similarly, although the bore 32 is also depicted as having circular cross-sectional shape, the bores in connector tubes used in the connection systems of the present invention may take any suitable shape (e.g., octagonal, elliptical, oval, etc.). Further, although the tube 30 and its bore 32 both have that same circular cross-sectional shapes, the bores and tubes may have different cross-sectional shapes. Also, although the bore 32 is depicted as centered within the tube 30, the bore 32 may alternatively be offset from the center of the tube 30. Also, although the tube 30 and its bore 32 are depicted as having a uniform cross-sectional size along the length of the tube 30, the connector tubes and/or bores therein may vary in size along the length of the tube. For example, the tube 30 may taper or narrow towards its ends.

Referring to FIG. 4, the connector tube 30 may be described as defining a tube axis 31 (whose end is seen in FIG. 4) that is centered within and extends through the tube 30. In the depicted embodiment, the tube 30 is offset from the longitudinal axis 12 of the body 20 such that the tube axis 31 is also offset from the longitudinal axis 12. Although the longitudinal axis 12 and the tube axis 31 are parallel to each other in the depicted embodiment, a parallel relationship between the longitudinal axis 12 and the tube axis 31 is not required.

The connector body 20 and the connector tube 30 may be formed as a one-piece completely integral component (by, e.g., machining, molding, casting, etc.) or, alternatively, the connector body 20 and the connector tube 30 may be independent components that are assembled together. For example, the connector tube 30 may be formed of one material that may be located within an aperture in a connector body 20 that is formed of a different material. The connector body 10 and/or the connector tube 30, or the components thereof, may be formed of any medically acceptable material, such as, but not limited to, a polymeric material, noble metals (e.g., titanium), stainless steel, Nitinol, etc. In some embodiments, the connector tube 30 may be insert-molded in the connector body 20. The connector tube 30 may, alternatively, be retained within the connector body 20 by a friction fit, an adhesive, etc.

Also, although the connector tube 30 is depicted as extending completely through the connector body 20, in some embodiments the tube 30 may not extend completely through the connector body 20. If the connector body 20 includes two or more connector tubes extending therefrom, each tube 30 may be a separate and independent article, with the different tubes being connected by passageways formed in the connector body.

The catheter connection system 10 depicted in FIGS. 1-5 also includes a collar 40. The collar 40 includes a cavity 42 sized and shaped to accept a portion of the connector body 20 and a passage 44 through which the connector tube 30 extending from the connector body 20 and a catheter 15 fitted over the tube 30 extend.

The collar 40 may have any selected exterior shape. It may be beneficial if the exterior shape of the collar 40 is tapered as shown to provide a smooth transition between the catheter 15 and the collar 40. Although not shown, the connection system 10 may include a boot or sleeve that extends over the connection system and the catheter proximate the connection system 10. Such a boot or sleeve may provide a smoother, more biocompatible surface and may provide some strain relief for the connections.

As discussed herein, the collar 40 includes a passage 44 in which the catheter 15 and the tube 30 are located when the connection system 10 is in use. The passage 44 extends from the cavity 42 in the collar 40 to the end 46 of the collar 40. The passage 44 in the collar 40 extends along a passage axis which, in the depicted embodiment, is coincident with the longitudinal axis 12, although in some embodiments, the axis of passage 44 may not be coincident with the longitudinal axis 12 defined by the connector body 20.

Although the depicted passage 44 has a circular cross-sectional shape, the passage in the collars 40 used in the connection systems of the present invention may take any suitable shape (e.g., octagonal, elliptical, oval, etc.). Also, although the passage 44 is depicted as centered within the collar 40, the passage 44 may alternatively be offset from a center of the collar 40. Further, although the passage 40 is depicted as having a uniform cross-sectional size along its length, the passages used in collars of the invention may vary in size along their lengths. For example, the passage 44 may taper or narrow towards the distal end 46 of the collar 40.

Figure 5:
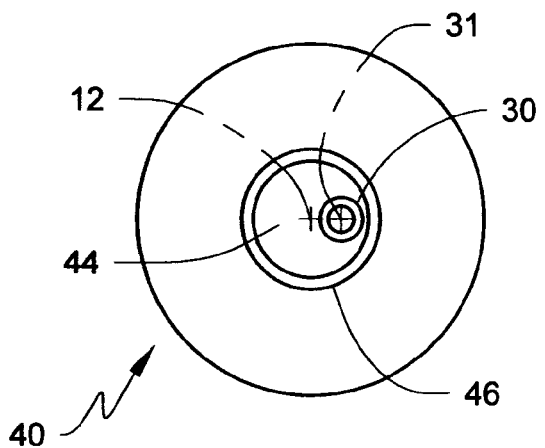
FIG. 5 is an end view of the collar engaged with the connector body of the catheter connection system of FIG. 1.

FIG. 5 is an end view of the collar 40 engaged with the connector body 20 when viewed from the distal end 46 of the collar 40. The catheter 15 is not depicted in FIG. 5 to more clearly show the relationship between the connector tube 30 and the passage 44 in the collar 40. In FIG. 5, the passage 44 is centered on the longitudinal axis 12 while the connector tube 30 (and, thus, its own axis 31) is offset from the longitudinal axis 12. Due to the offset positioning of the connector tube 30 within the passage 44, a portion of the outer surface of the connector tube 30 is closer to one side of the inner surface of the passage 44.

When a catheter fitted over the connector tube 30 is located within the passage 44 (see, for example, FIG. 2), the end portion of the catheter is differentially compressed on its opposing sides between the outer surface of the connector tube 30 and the inner surface of the passage 44. In other words, the end portion of the catheter 15 that is occupied by the connector tube 30 where the connector tube 30 and collar bore 44 are closest may be compressed to a greater degree than the portion of the catheter on the opposite side of the tube 30 (i.e., where the connector tube 30 and passage 44 are furthest apart from each other). That differential compression may increase the holding force for securing the catheter connection under cyclic force action, etc. Although not depicted, it should be understood that the tube 30 and/or the portion of the collar 40 containing the passage 44 may deflect in response to the forces experienced by both components.

Also, although the passage 44 is depicted as being centered on the longitudinal axis 12 while the connector tube 30 is offset from that axis, in some embodiments the connector tube 30 may be centered on the longitudinal axis 12 while the passage 44 in collar 40 is offset from the longitudinal axis 12. In still other embodiments, both the connector tube 30 and the passage 44 in the collar 40 may be offset from the longitudinal axis 12. It may be beneficial, however, if the connector tube 30 and the passage 44 are offset from each other to provide the desired differential compression of a catheter. It may be helpful if the axis along which the passage 44 extends and the tube axis 31 (along which the tube 30 extends) are parallel, but such an arrangement may not be required.

It may be advantageous if the end portion of the catheter 15 that is occupied by the connector tube 30 is located entirely within the cavity 42 and passage 44. In other words, the distal end of the tube 30 (the end furthest from the connector body 20) may best be located within the passage 44 when the collar 40 is properly positioned on the connector body 20. Such an arrangement may reduce the likelihood that the tube 30 will tear or otherwise perforate the catheter 15 during use.

Figure 3:
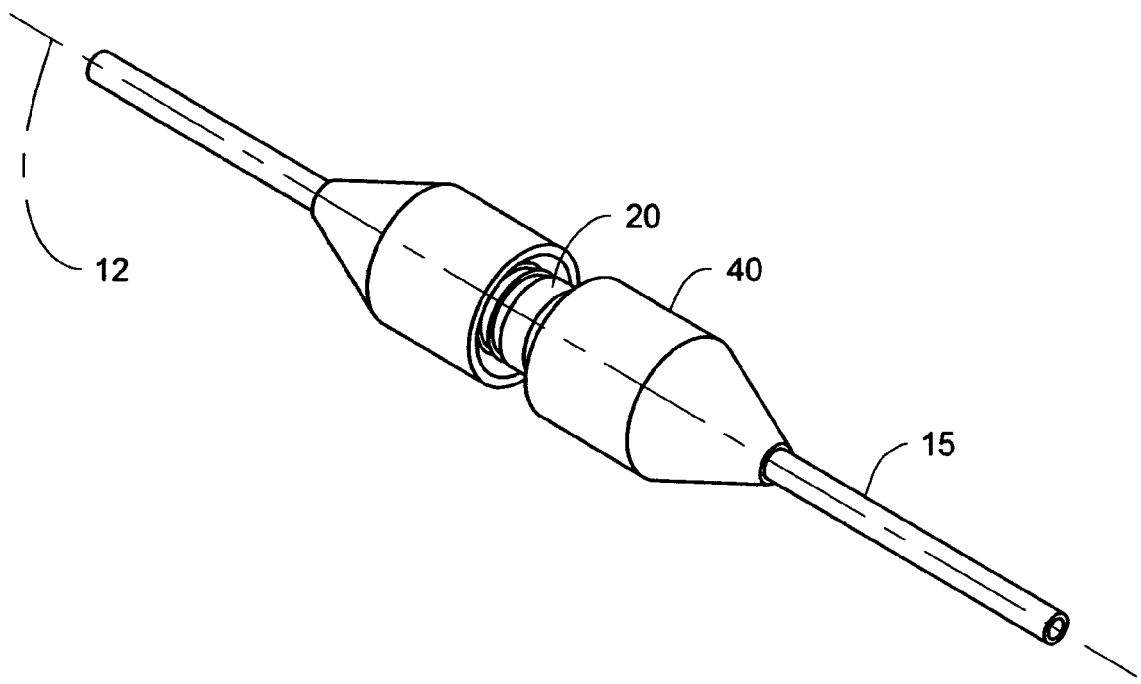
FIG. 3 is perspective view of the catheter connection system of FIG. 1.

The catheter connection system 10 may also include some type of retention mechanism for retaining the collar 40 on the connector body 20 (as depicted in, e.g., FIGS. 1-3). Any suitable technique may be used to attach the collars to the connector bodies. One example of a ratchet mechanism is depicted in FIGS. 1 & 2, wherein the outer surface of the connector body 20 includes ridges 28 to form a ridged outer surface 22 that cooperates with a ridged surface formed by ridges 48 in the cavity 42 of the collar 40 to retain the collar 40 on the connector body 20.

Although the retention mechanism depicted in FIGS. 1 & 2 is a ratcheting connection, other retention mechanisms may be used to retain the collar 40 on the connector body 20, such as, but not excluding, a threaded connection, a friction fit, an adhesive, detents, etc.

The catheter connection systems of the present invention may have any suitable dimensions depending on the sizes of the catheters to be connected. For illustrative purposes only, the following dimensions may be used in connection with the various components used in the catheter connection systems, although it should be understood that connectors constructed with dimensions outside of these exemplary ranges may still fall within the scope of the present invention. These dimensions will be expressed in terms of diameter, although it should be understood that the term "diameter" may refer to effective diameter (greatest cross-sectional dimension) of any component, whether it is circular or non-circular cross-sectional shape.

The outer diameter of the connector body 20 may be about 2 millimeters (mm) to about 5 mm. The length (extending longitudinally along axis 12) of the connector body 20 may be about 0.8 centimeters (cm) to about 1.5 cm. The outer diameter of the connector tube 30 may be about 0.4 mm to about 0.8 mm and the inner diameter of the bore formed therein may be about 0.2 mm to about 0.4 mm. The connector tube 30 may extend out of the connector body 20 by a distance of about 0.5 centimeters (cm) to about 1 cm. With respect to the collar 40, the passage 44 may have a diameter of about 0.5 mm to about 1 mm. The depth (i.e., the distance extending inward from the proximal end of the cavity 42 to the collar stop surface 46) may be about 5 mm to about 15 mm. The length of the passage 44 and the collar 40 overall may be such that the distal end 46 of the collar is located about 5 mm or more past the end of the tube 30.

Catheter bodies that may be useful in connection with connectors such as, e.g., the offset connectors described herein may possess a number of features or characteristics. For example, catheters may be constructed such that they conform to the shape of the connector inserted into the proximal end of the lumen to form a fluid-tight seal between the outer surface of the connector and the inner surface of a lumen into which the connector is inserted. As used herein, a "fluid-tight seal" means a seal that prevents the passage of fluids delivered through the catheter when implanted into the body of a subject (it being understood that almost any seal can be compromised by the application of fluid pressure beyond the intended working limit of the seal). After, for example, a connector tube (such as, e.g., connector tube 30) is inserted into a catheter lumen, catheter may generally conform to the shape of the connector tube 30 and the surrounding passage 44 in the collar 40 to form a fluid-tight seal between the catheter and the connector.

The reinforcing braid and optional outer jacket on catheters that may be beneficially used in connection with the present invention may also provide improvements in crush resistance, kinking, elongation, etc. These enhanced physical characteristics may be particularly helpful in catheters that include elastically compressible inner bodies that, themselves, have significantly limited ability to resist crushing, kinking, elongation, etc.

Figure 6:
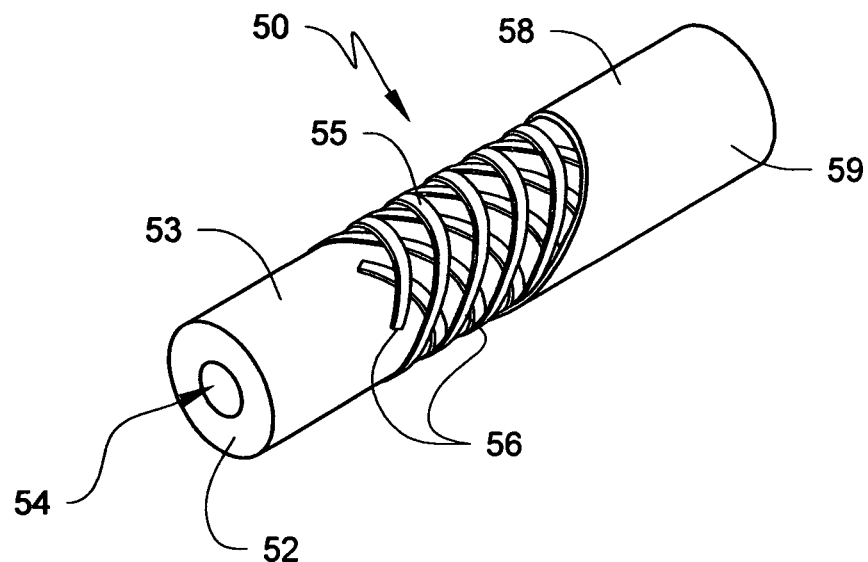
FIG. 6 is a perspective view of one illustrative catheter body construction that may be used with the catheter connection system of the present invention (with layers partially removed).
Figure 7:
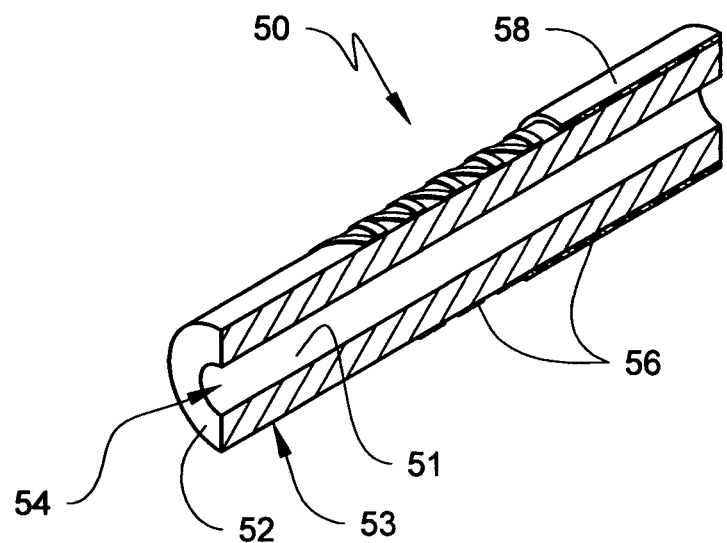
FIG. 7 is a cross-sectional view of FIG. 6 taken along the bore depicted in FIG. 6.

FIGS. 6 & 7 depict views of a portion of one exemplary catheter that may be suitable for use in connection with the offset catheter connector (e.g., offset catheter connector 20 of FIG. 1) of the present invention. The portion of the catheter 50 that is depicted in FIG. 6 includes an inner body 52, a reinforcing braid 55, and an optional outer jacket 58 that covers the reinforcing braid 55 and the outer surface 53 of the inner body 52.

The inner body 52 of the catheter 50 defines a lumen 54 that extends from the proximal end of the catheter 50 to an infusion section or other portion of the catheter 50 to which fluids are to be delivered using the lumen 54. In many embodiments, the lumen 54 will extend to the distal end or near to the distal end of the catheter 50. The inner body 52 of the catheter 50 can be described as including a wall that extends from an inner surface 51 to an outer surface 53. The lumen 54 is defined by the inner surface 51 of the inner body 52.

The catheter 50 also includes a reinforcing braid 55 located around the outer surface 53 of the inner body 52. The reinforcing braid 55 may include two or more strands 56 that are wound and/or woven around the outer surface 53 of the inner body 52. The spacing between the reinforcing strands 56 may be constant or it may change along the longitudinal length of the catheter 50. The helix angle (i.e., the angle between the strands 56 and a longitudinal axis extending through, e.g., lumen 54) may remain constant or it may change along the longitudinal length of the catheter 50.

The optional outer jacket 58 is attached to the outer surface 53 of the inner body 52 over the reinforcing braid 55. The outer jacket 58 may be provided to present a smoother outer surface 59 for the catheter 50 than could be provided if the reinforcing braid 55 were exposed on the outer surface 53 of the inner body 52.

The reinforcing braid 55 and optional outer jacket 58 may improve the dimensional stability of the catheter 50 both longitudinally as well as radially. For example, the reinforcing braid 55 and optional outer jacket 58 may limit elongation of the catheter 50 along its length (where length is the dimension along which the lumen 54 extends). The reinforcing braid 55 and optional outer jacket 58 may also limit radial expansion of the inner body 52 due to, e.g., the insertion of a connector, fluid pressure within the lumen 54, etc. Other features that may potentially be provided by the reinforcing braid 55 and optional outer jacket 58 may be improved resistance to kinking, crushing, etc. The reinforcing braid 55 and optional outer jacket 58 may also assist in improving the ability of the catheter 50 to transmit torque along its length.

The various components of the catheter 50 may possess a variety of characteristics. For example, the inner body 52 may be an elastically compressible inner body 52, wherein the wall of the inner body 52 is elastically compressible when compressed by, e.g., a connector inserted into the lumen 54 in the inner body 52. The inner body 52 may compress and conform to the shape of a connector such that a fluid-tight seal is created between the exterior of the connector and the interior surface 51 of the inner body 52. In one manner, the elastic compressibility of the inner body 52 may be characterized in terms of the durometer of the material used to construct the inner body 52. For example, the inner body 52 may be constructed of material that has a durometer of about 20 Shore A to about 55 Shore D.

As used herein, "elastically compressible" (and variations thereof) means that the wall of the inner body can be compressed from its original uncompressed dimension and, after compression of about 25% (where the distance between the inner surface 51 and the outer surface 53 is about 75% of its original dimension), the thickness of the wall between the inner surface 51 and the outer surface 53 elastically returns to at least about 95% of its original dimension within a time period of about five (5) minutes or less after the compressive force is removed. For example, if a portion of an inner body wall with an original thickness of about 0.100 mm were compressed to a thickness of about 0.075 mm, the compressed portion of the wall would recover to a thickness of about 0.095 mm or more within a period of five (5) minutes or less after the compressive force was removed.

A variety of materials may be used to provide an elastically compressible inner body 52, although the materials selected may preferably be suitable for use in medical devices. Examples may include, e.g., silicone, polyurethane, silicone-urethane thermoplastic copolymer, etc. Also, although the inner body 52 is depicted as being a substantially homogeneous body, it may alternatively be constructed of two or more materials (arranged in layers, as a dispersion, etc.). In some embodiments, the inner body 52 may consist essentially of a medical grade silicone.

Similarly, a variety of materials may be used to construct the reinforcing braid 55. The strands 56 may be inelastic such that they are substantially inextensible under the stresses encountered in normal, expected use of the catheter 50. By "inelastic" (and variations thereof), it is meant that, after elongation of about 10% or more along the length of the strand 56, the strand will recover about 50% or less of the elongation. For example, if an inelastic strand with an original length of 1 centimeter (cm) were stretched to a length of 1.1 cm, the strand would only recover (after removal of the tension force) to a length of 1.05 cm or greater.

Although depicted as monofilaments, each of the strands 56 may alternatively be a composite of two or more filaments. The materials used to construct the strands may include, e.g., polymers (e.g., polyester (PEN or PET)), metals (e.g., stainless steel, Nitinol, etc.), composite materials, etc. Polymers such as, e.g., polyesters, may provide the desired strength while maintaining a higher level of flexibility than may be possible if, e.g., metallic strands are used. The strands 56 forming the reinforcing braid 55 may be constructed of the same materials or different materials. In one embodiment, the strands 56 may be constructed of PEN or PET (a polyester) and have a cross-sectional dimension (e.g., diameter) of about 0.025 mm to about 0.05 mm. Although the strands 56 used to construct the reinforcing braid may be the same size, they may alternatively be of different sizes.

The materials used for the outer jacket 58 may also potentially be inelastic, although this characteristic is not required. It may, however, be beneficial if the material present on the outer surface 59 of the outer jacket 58 is biocompatible, hydrophobic, and possess a relatively high tensile strength. One example of a potentially suitable material for the outer jacket 58 is a silicone-urethane thermoplastic copolymer (such as PURSIL 20 or PURSIL 35, available from The Polymer Technology Group, Inc., Berkeley, Calif.). Other potentially useful materials for the outer jacket 58 may include, e.g., polyurethane (e.g., polyurethane 80A or 55D), etc.

Although the outer jacket 58 is depicted as be constructed of a single layer of material, the outer jacket 58 may alternatively be constructed as a composite material of, e.g., two or more layers, a dispersion, etc. For example, an outer jacket 58 may be constructed of a first material that is coated with a second material to, e.g., improve its biocompatibility, reduce surface energy, etc.

In some embodiments, the reinforcing braid 55 may span the entire length of the inner body 52 (i.e., from its proximal to its distal end). In other embodiments, the reinforcing braid 55 may terminate at a location that is between the distal end of the inner body and the proximal end of the inner body such that a section of inner body 52 located at the distal end of the inner body 52 and extending in the proximal direction is free of the reinforcing braid 55. In some embodiments, the reinforcing braid 55 may be present only over the end portion of the inner body 52 that is occupied by a connector (e.g., a tube 30) inserted into the lumen 54.

Although the reinforcing braid 55 may terminate short of the distal end of the catheter 50, the outer jacket 58 may extend from the proximal end of the catheter 50 all the way to the distal end of the catheter 50 to protect the outer surface 53 of the inner body 52 over its entire length.

The catheter 50 preferably has a construction in which the outer dimensions (e.g., the diameter in the case of catheter 50 with a circular shape such as that depicted in FIG. 6) remain substantially constant when, e.g., a connector tube 30 is inserted into the lumen 54 of the inner body. Because the reinforcing braid 55 is essentially inextensible and the inner body 52 is elastically compressible, the insertion of a connector into the inner lumen 54 may cause the inner body 52 to conform to the shape of the connector in a manner that forms a fluid-tight seal between the interior surface 51 of the inner body 52 and the outer surface of the connector inserted into the lumen 54. When present, the optional outer jacket 58 may assist in restraining expansion of the inner body 52 in response to the insertion of a connector into the lumen 54.

Although the catheter 50 is depicted as having a generally uniform cross-sectional size along its length, catheter bodies used in connection with the invention may vary in size along their length, e.g., their cross-sectional dimensions may decrease when moving towards the distal ends of the catheter bodies. Likewise, the lumens in catheter bodies of the invention may also have a uniform cross-sectional size over their entire lengths or they may change.

The dimensions of the catheters (and their components) may vary depending on the uses for which they are designed. Although the catheter 50 depicted in FIGS. 6 & 7 has a circular cross-sectional shape, any suitable shape may alternatively be used (e.g., octagonal, elliptical, oval, etc.). For exemplary purposes only, the catheters of the present invention may include inner bodies 52 with an inner diameter (i.e., the diameter of the lumen 54) of about 0.6 mm to about 0.7 mm and outer diameters of about 0.9 mm to about 1.2 mm. The outer jacket 58 may have an outer diameter (which corresponds to the outer diameter of the catheter 50 as a whole) of about 1.4 mm and wall thickness of about 0.1 mm. These dimensions are provided for illustrative purposes only and it should be understood that catheters constructed with dimensions outside of these exemplary ranges may still fall within the scope of the present invention.

At least in one embodiment, the catheter 50 may be expanded or contracted at particular locations along its length, as in the well-known child's "finger trap," once known as a "Chinese finger trap." The distal end of the catheter 50 may be fitted over the connector tube 30. If the catheter is then subjected to tension by pulling it away from the connector body 20, the tension may cause a reduction in the inner diameter of the catheter 50, thus causing the catheter 50 to grip the tube 30 even more forcefully.

Figure 8:
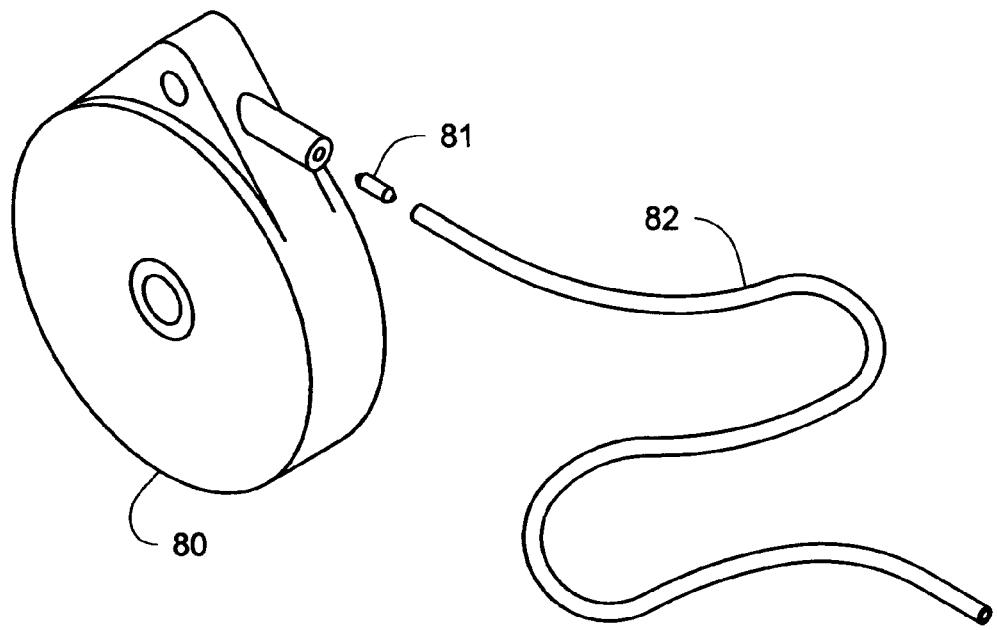
FIG. 8 depicts one illustrative embodiment of an implantable medical device, a delivery catheter, and a catheter connection system of the present invention.

FIG. 8 depicts one illustrative embodiment of an implantable therapeutic substance delivery device 80 that may be used with an offset catheter connector 81 and a delivery catheter 82 attached to the device 80 using the offset catheter connector 81. The offset catheter connector 81 is connected directly to an outlet port on the device 80 and the delivery catheter 82 is attached to the offset catheter connector 81.

The therapeutic substance delivery device 80 can be used for a wide variety of therapies such as pain, spasticity, cancer, and many other medical conditions. The implantable therapeutic substance delivery device 80 is typically implanted by a clinician in a sterile surgical procedure performed under local, regional, or general anesthesia. Before implanting the therapeutic substance delivery device 80, a delivery catheter 82 is typically implanted with the distal end positioned at the desired therapeutic substance delivery site and the proximal end tunneled to the location where the therapeutic substance delivery device 80 is to be implanted. Then, the therapeutic substance delivery device 80 may be connected to the proximal end of the delivery catheter 82 using the offset catheter connector 81.

The therapeutic substance delivery device 80 may operate to infuse a therapeutic substance into a patient. Potentially suitable examples of therapeutic substance delivery devices that may be used in connection with the present invention may include, but are not limited to, powered pump assemblies (e.g., piston pumps, diaphragm pumps, peristaltic pumps, etc.) or they may be activated based on pressure to drive fluid out of a reservoir (e.g., using collapsing diaphragms, expanding bladders, etc.). Examples of some potentially suitable therapeutic substance delivery devices may include, e.g., commercially available implantable infusion pumps such as, for example, the SYNCHROMED EL pumps, Models 8626 and 8627, manufactured by Medtronic, Inc., Minneapolis, Minn.

The "therapeutic substance" delivered is a product or substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

Figure 9:
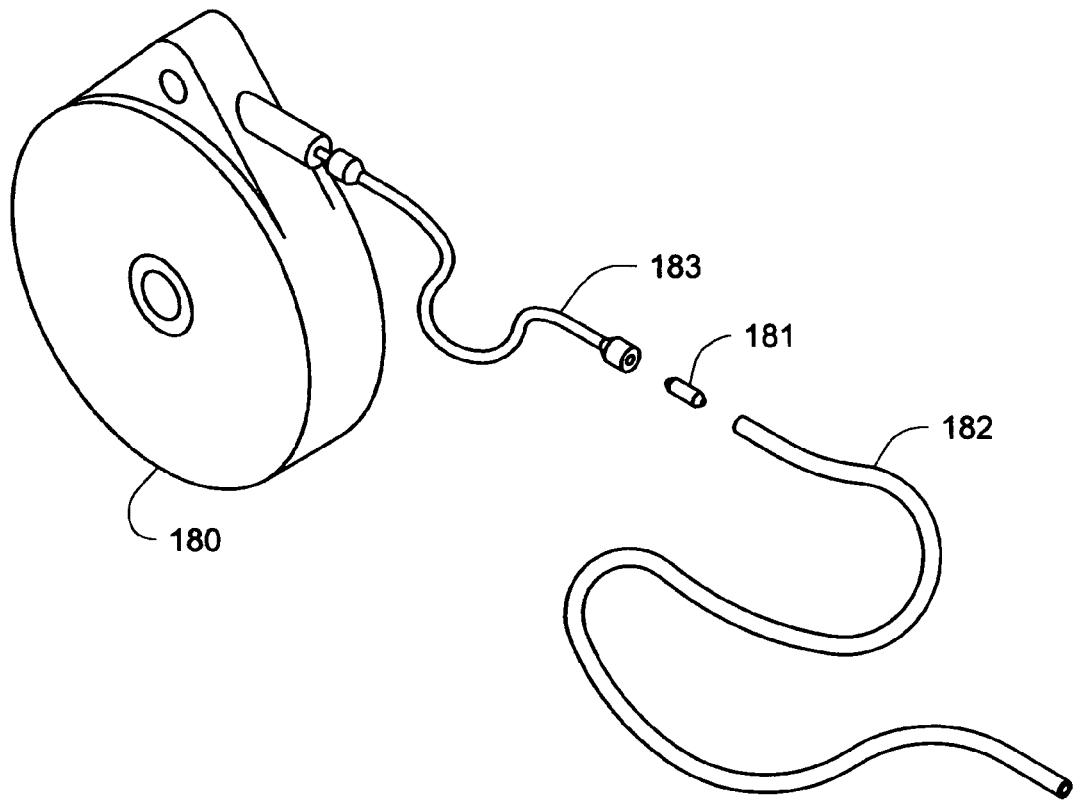
FIG. 9 depicts another illustrative embodiment of an implantable medical device connected to a proximal catheter connected, a delivery catheter and a catheter connection system of the present invention.

FIG. 9 depicts an alternative embodiment of an implantable therapeutic substance delivery device 180, a proximal catheter 183, a delivery catheter 182, and an offset catheter connector 181 according to the present invention. In this embodiment, one end of the proximal catheter 183 is connected to the therapeutic substance delivery device 180. The other end of the proximal catheter may be connected to the delivery catheter 182 using the offset catheter connector 181. In embodiments where both sides of the connector 181 are offset, it may be beneficial if the ends of the proximal catheter 183 and the delivery catheter 182 attached to the connector 181 have elastically compressible inner bodies and the other features described herein.

The complete disclosure of the patents, patent documents, and publications cited herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A catheter connection system comprising:
   a connector body;
   a first tube extending from the connector body, wherein the first tube comprises a bore extending through the first tube, and wherein the first tube defines a first tube axis centered within and extending through the first tube;
   a first catheter comprising an end portion attached to the first tube, wherein the end portion of the first catheter comprises a lumen that is occupied by the first tube; and
   a first collar attached to the connector body, wherein the first collar comprises a first passage, wherein the first passage defines a first passage axis centered within and extending through the first passage, and wherein the end portion of the first catheter and the first tube are located within the first passage, and wherein the first passage axis is offset from the first tube axis when the first collar is attached to the connector body;
   wherein the end portion of the first catheter is differentially compressed on opposing sides between a portion of an outer surface of the first tube and a portion of an inner surface of the first passage.

2. A system according to claim 1, wherein the first tube axis is parallel to the first passage axis.

3. A system according to claim 1, wherein the bore in the first tube is centered along the first tube axis.

4. A system according to claim 1, wherein the connector body comprises a circular cylindrical connector body defining a central axis, and wherein the first tube axis is offset from the central axis.

5. A system according to claim 1, wherein the connector body comprises a circular cylindrical connector body defining a central axis, and wherein the first passage axis is coincident with the central axis when the first collar is attached to the connector body.

6. A system according to claim 1, wherein the first tube comprises a uniform cross-sectional profile along its length.

7. A system according to claim 1, wherein the first passage in the first collar comprises a uniform cross-sectional profile along its length.

8. A system according to claim 1, wherein the first tube is located entirely within the first passage when the first collar is attached to the connector body.

9. A system according to claim 1, wherein the connector body and the first collar comprise a retention mechanism located between the first collar to the connector body.

10. A system according to claim 9, wherein the retention mechanism comprises a ratchet connection.

11. A system according to claim 1, wherein the lumen in the proximal end of the catheter is located within an elastically compressible inner body that is surrounded by a reinforcing braid located around an outer surface of the inner body, and further wherein the reinforcing braid and the inner body are surrounded by an outer sheath covering the outer surface of the inner body and the reinforcing braid, wherein the inner body is differentially compressed between the first tube and the first passage.

12. A system according to claim 1, the system comprising:
    a second tube extending from the connector body, wherein the second tube comprises a bore extending through the second tube, and wherein the second tube defines a second tube axis centered within and extending through the second tube;
    a second catheter comprising an end portion attached to the second tube, wherein the end portion of the second catheter comprises a lumen that is occupied by the second tube; and
    a second collar attached to the connector body, wherein the second collar comprises a second passage, wherein the second passage defines a second passage axis centered within and extending through the second passage, and wherein the end portion of the second catheter and the second tube are located within the second passage, and wherein the second passage axis is offset from the second tube axis when the second collar is attached to the connector body;
    wherein the end portion of the second catheter is differentially compressed on opposing sides between a portion of an outer surface of the second tube and a portion of an inner surface of the second passage.

13. A system according to claim 12, wherein the first tube and the second tube are aligned such that the first tube axis and the second tube axis are coincident with each other.

14. A system according to claim 12, wherein the first tube and the second tube comprise portions of a common tube that extends through the connector body.

15. A system according to claim 12, wherein the second tube axis is parallel to the second passage axis.

16. A system according to claim 12, wherein the bore in the second tube is centered along the second tube axis.

17. A system according to claim 12, wherein the connector body comprises a circular cylindrical connector body defining a central axis, and wherein the second tube axis is offset from the central axis.

18. A system according to claim 12, wherein the connector body comprises a circular cylindrical connector body defining a central axis, and wherein the second passage axis is coincident with the central axis when the second collar is attached to the connector body.

19. A system according to claim 12, wherein the second tube comprises a uniform cross-sectional profile along its length.

20. A system according to claim 12, wherein the second passage in the second collar comprises a uniform cross-sectional profile along its length.

21. A system according to claim 12, wherein the second tube is located entirely within the second passage when the second collar is attached to the connector body.

22. A system according to claim 12, wherein the connector body and the second collar comprise a retention mechanism located between the second collar to the connector body.

23. A system according to claim 22, wherein the retention mechanism comprises a ratchet connection.

24. A system according to claim 12, wherein the lumen in the proximal end of the catheter is located within an elastically compressible inner body that is surrounded by a reinforcing braid located around an outer surface of the inner body, and further wherein the reinforcing braid and the inner body are surrounded by an outer sheath covering the outer surface of the inner body and the reinforcing braid, wherein the inner body is differentially compressed between the first tube and the first passage.

25. A method of connecting a catheter to a connection system, the method comprising:
    inserting a first tube into a lumen at an end of a first catheter such that the first tube occupies an end portion of the catheter, wherein the first tube extends from a connector body, and further wherein the first tube comprises a bore extending through the first tube and a first tube axis centered within and extending through the first tube; and differentially compressing opposing sides of the catheter within the end portion of the catheter by attaching a first collar to the connector body, wherein the compression occurs between the first tube and a first passage of the first collar, wherein the first passage defines a first passage axis centered within and extending through the first passage, and wherein the end portion of the first catheter and the first tube occupying the end portion of the first catheter are located within the first passage, and wherein the first passage axis is offset from the first tube axis when the first collar is attached to the connector body.

26. A method according to claim 25, wherein the first tube is located entirely within the first passage when the first collar is attached to the connector body.

27. A therapeutic substance delivery system comprising:
an implantable therapeutic substance delivery device;
a delivery catheter; and
a catheter connector connecting the delivery catheter to the implantable therapeutic substance delivery device, wherein the catheter connector comprises:
   a connector body;
   a first tube extending from the connector body, wherein the first tube comprises a bore extending through the first tube, and wherein the first tube defines a first tube axis centered within and extending through the first tube, wherein an end portion of the delivery catheter comprises a lumen that is occupied by the first tube; and
   a first collar attached to the connector body, wherein the first collar comprises a first passage, wherein the first passage defines a first passage axis centered within and extending through the first passage, and wherein the end portion of the delivery catheter and the first tube are located within the first passage, and wherein the first passage axis is offset from the first tube axis when the first collar is attached to the connector body;
   wherein the end portion of the delivery catheter occupied by the first tube is differentially compressed on opposing sides between a portion of an outer surface of the first tube and a portion of an inner surface of the first passage.

28. A system according to claim 27, wherein the system further comprises a proximal catheter located between the implantable therapeutic substance delivery device and the catheter connector, wherein the catheter connector further comprises:
   a second tube extending from the connector body, wherein the second tube comprises a bore extending through the second tube, and wherein the second tube defines a second tube axis centered within and extending through the second tube, and wherein an end portion of the proximal catheter comprises a lumen that is occupied by the second tube; and
   a second collar attached to the connector body, wherein the second collar comprises a second passage, wherein the second passage defines a second passage axis centered within and extending through the second passage, and wherein the end portion of the proximal catheter and the second tube are located within the second passage, and wherein the second passage axis is offset from the second tube axis when the second collar is attached to the connector body;
wherein the end portion of the proximal catheter occupied by the second tube is differentially compressed on opposing sides between a portion of an outer surface of the second tube and a portion of an inner surface of the second passage.

* * * * *